United States Patent [19]

Yabe

[11] 4,075,074
[45] Feb. 21, 1978

[54] METHOD FOR PREPARING BENZO[C]CINNOLINE AND ITS DERIVATIVES

[75] Inventor: Akira Yabe, Fujisawa, Japan

[73] Assignee: Agency of Industrial Science & Technology, Tokyo, Japan

[21] Appl. No.: 777,419

[22] Filed: Mar. 14, 1977

[30] Foreign Application Priority Data

June 7, 1976    Japan .................................. 51-066258

[51] Int. Cl.$^2$ ............................................... B01J 1/10
[52] U.S. Cl. ................................................. 204/158 R
[58] Field of Search ..................................... 204/158 R

[56] References Cited

U.S. PATENT DOCUMENTS 3,666,643    5/1972    Inaba et al. ....................... 204/158 R

*Primary Examiner*—Howard S. Williams
*Attorney, Agent, or Firm*—Armstrong, Nikaido & Marmelstein

[57] ABSTRACT

Benzo[C]cinnoline or its derivative is prepared by irradiating 2,2'-diazidobiphenyl or its derivative with light in a low-temperature rigid solvent.

9 Claims, No Drawings

METHOD FOR PREPARING BENZO[C]CINNOLINE AND ITS DERIVATIVES

BACKGROUND OF THE INVENTION

Benzo[C]cinnoline and its derivatives have been used in various fields, for instance, as raw materials for useful fine chemicals. There have been known the following three routes of preparing the benzo[C]cinnolines by using different starting materials, respectively.

The first route contains methods of reducing 2,2'-dinitrobiphenyls, in which the reduction is conducted by electrolytic reduction in diluted ethanol or by using a reducing agent such as triethyl phosphite, triphenyl phosphine, sodium amalgam or the like. According to these reduction methods, by-products are produced in large quantities and the yields of the benzo[C]cinnolines are at most about 10 – 50%.

The second route is of using 2,2'-diaminobiphenyls as starting materials, which are converted to the corresponding diazonium salts and then subjected to Sandmeyer reaction using bromides or the like. According to these methods, the yields of the benzo[C]cinnolines are at most about 50% and carbazoles are produced as by-products.

The third route is of using azobenzenes as starting materials, which are reacted with aluminum chloride in the presence of sodium chloride or irradiated with light in concentrated sulfuric acid or aqueous solution containing ferric chloride. According to these methods, the yields of the benzo[C]cinnolines are at most about 45%.

Above mentioned conventional methods have such disadvantages that the yields of the objective compounds are about 50% or less, by-products are produced in large quantities and many steps are required in order to separate and purify the objective compounds.

An object of the present invention is to solve such conventional disadvantages.

An other object of the present invention is to provide a method for preparing benzo[C]cinnoline and its derivatives with high yields.

A further object of the present invention is to provide a method for preparing benzo[C]cinnoline and its derivatives with high yields by using 2,2'-diazidobiphenyl and its derivatives as starting materials and utilizing photo-reaction.

The foresaid objects and other objects and advantages of the present invention will become more apparent from the following description.

SUMMARY OF THE INVENTION

The objects of the present invention are achieved by irradiating 2,2'-diazidobiphenyl or its derivative with light in a low-temperature rigid solvent and thereby the objective compounds, benzo[C]cinnoline or its derivative, is selectively prepared with high yield.

PREFERRED EMBODIMENT OF THE INVENTION

The starting compounds to be used in the present invention are 2,2'-diazidobiphenyl and its derivatives and shown by the following general formula;

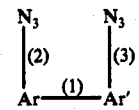

wherein Ar and Ar' represent same or different aromatic groups and the bonds (2) and (3) each is present at the 2-position (ortho position) or aromatic ring, respectively, to the bond (1) which links aromatic groups each other. Ar and Ar' may be selected from any kind of aromatic groups such as benzene ring, naphthalene ring or 6-membered aromatic ring containing 1 – 3 of nitrogen atoms and also may contain one or more substituents optionally.

Any kind of substituents which do not have a bad effect on the reaction may be used. Preferable substituents are hydrocarbon group such as alkyl, nitro group, carboxyl group, halogen atoms, alkoxy group, acyl group, cyano group, sulfonic acid group and the like. These substituents may be contained up to 8 in a molecule.

Typical compounds to be used as starting compounds in the present invention are as follows;

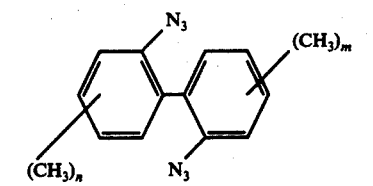

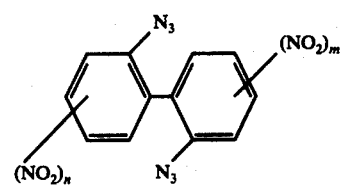

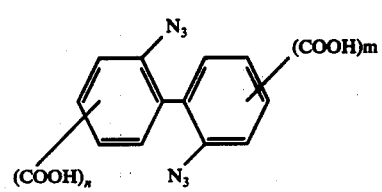

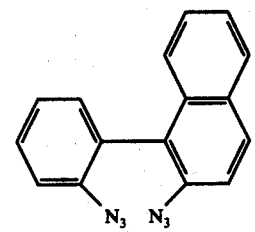

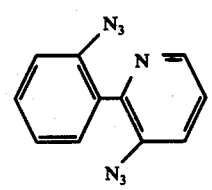

-continued

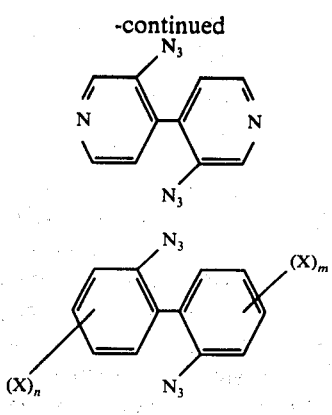

wherein m and n integers of 0 to 4, respectively, and X represents halogen atom.

Low-temperature rigid solvents which are necessarily used in the present invention are, as well known, defined as solvents which, when dissolved solutes at room temperature and cooled thereafter, can become gradually viscous in the state of glass with lowering the temperature and be finally solidified transparently, not crystallized.

Preferable low-temperature rigid solvents are as follows; n-pentane, petroleum ether, diethyl ether, ethanol, methanol, propanol, 2-bromobutane, a mixture of ethanol and methanol (ethanol: methanol = 5 : 1 – 9 : 1), ethanol : glycerol (11 : 1), ethanol : diethyl ether (2 : 1), ethanol : water (<20 : 1), ethanol : equeous solution of 0.5% NaOH (<20 : 1), ethanol : diethyl ether : isopentane (2 : 5 : 5), ethyl cellosolve : n-butanol : n-pentane (1 : 10 – 2 : 10), n-pentane : n-heptane (1 : 1), methyl cyclotexane : n-pentane (4 : 1 – 2 : 2), n-propyl ether : n-pentane (2 : 1), iso-pentane : 3-methyl pentane (any mixing ratios), glycerol, glycerol triacetate, glycerol tributyrate and 2,5-dimethyl pyridine.

The method of the present invention may be conducted by dissolving the starting compound in the low-temperature rigid solvent at room temperature and cooling the system, for instance, by means of contacting with a coolant till the viscosity of the system becomes at least $10^3$ poise and then by irradiating thereto with light.

The concentration of the starting compound in the low-temperature rigid solvent is preferably less than about 5% by weight and more preferably about 0.01 – 1% by weight.

The cooling temperature is preferably a temperature at which the viscosity of system becomes as high as possible and is usually decided in the range of about −50° C – −200° C in accordance with a selected solvent. For instance, in case of using a mixture of isopentane and 3-methyl pentane as a solvent, liquid nitrogen is preferably used as a coolant.

Reactors of the internal irradiation type or of the external irradiation type can be used. External irradiation type reactors having an irradiation surface made of quarty glass is more preferably used. Of cource, reactors made of conventional glass may also be used.

Various light sources such as low-pressure mercury arc lamp, medium-pressure mercury arc lamp, high-pressure mercury arc lamp, super high-pressure mercury arc lamp, high-pressure xenon arc lamp and the like can be used. The most preferable light source may be selected in accordance with the absorption spectrum of starting compounds to be used.

The optimum wavelength varies somewhat with the starting compounds. However, usually it is preferable to use the light sources which are capable of irradiating with light of wavelength of from about 200 nm to about 800 nm. Usually, it is most preferable to use a reactor made of quarty glass and low-pressure mercury arc lamp. The reaction time or the irradiation time varies with absorption efficiency of the starting compound, quantum yield in the photolytic reaction, spectrum and intensity of the light source, volume of the reactor and other factors, however, it is usually within 1 – 3 hours.

After sufficient irradiation, the reaction mixture is taken out of the coolant and the temperature is returned to room temperature to melt the rigid solvent. The reactant in the fluid solvent may be separated and purified in the usual ways. It is more preferable to purify the objective compounds by means of recrystallization or distillation.

The starting compounds of the present invention are azido compounds which can be prepared quite easily. They can be prepared from the corresponding amino compounds. For instance, the amino compounds are converted to the corresponding diazonium salts in the usual way and then mixed with sodium azide to promptly and selectively produce the objective azido compounds.

The method of the present invention can be handled quite easily just by projecting light in a low-temperature rigid solvent containing the starting compound and the treatment thereafter is also quite easy. Different from in the conventional reduction or oxidation methods, the reaction is not prevented by substituents in molecule at all in the method of the present invention. Therefore, according to the method of the present invention, various derivatives having substituents which are difficult to prepare by the conventional methods may be easily prepared.

The method of the present invention shows various advantages that the amounts of by-products may be very small and the objective compounds may be produced almost selectively and quantitatively. Moreover, according to the method of the present invention, the yields of the objective compounds having substituents are not so lowered as in conventional thermal reactions. In case of preparing such a derivative, the yields of the objective compounds in the present invention may be 2 – 5 times as high as in the conventional thermal reactions. According to the method of the present invention, it is quite easy to separate and purify the objective compounds from the reaction mixtures.

According to the present invention, benzo[C]cinnoline and its derivatives which may be used as intermediates for various fine chemicals are prepared with high yields and high purity from 2,2'-diazidobiphenyl and its derivatives, respectively.

The present invention is explained in detail by way of the following examples.

EXAMPLE 1

160 mg of 2,2'-diazidobiphenyl was dissolved in a mixed solvent (500 ml) of ethyl alcohol : diethyl ether : isopentane (2 : 5 : 5) and the resultant solution was poured into a quarty cylindrical cell. The cell was dipped in liquid nitrogen to convert the solution to low-temperature rigid solution.

The cell was irradiated with light for 2 hours by means of two low-pressure mercury arc lamps each of which is 30W and surrounded with a dewar vessel made of transparent quarty. After the irradiation, the cell was taken out of the coolant into room temperature to fluidize the solution. The reaction solution was transferred into an evaporator and the solvent was removed off by distillation at a temperature below 100° C. 120mg of the crystal was obtained.

The crystal had a melting point of 157° – 159° C and was identified with benzo[C]cinnoline in comparison with an authentic sample as to infrared spectrum, ultraviolet spectrum and the like. The yield was more than 98%.

EXAMPLE 2

180 mg of 2,2'-diazido-6,6'-dimethylbiphenyl was dissolved in a mixed solvent of isopentane : 3-methyl pentane (3 : 2) and then the solution thus obtained was treated in the same manner set forth in Example 1.

After irradiating and distilling, 142 mg of the crystal was obtained. The crystal was recrystallized using a mixed solvent of diethyl ether and hexane and 86 mg of pure 1,10-dimethyl benzo[C]cinnoline was obtained. Yield was 60%.

Analysis results.

m.p. 110 – 111° C

IR (KBr); 3080 – 3000, 1505, 1572, 1460, 1442, 1420, 1385, 1335 cm$^{-1}$

UV (MeOH); 331 ($\epsilon$ = 8900), 252 ($\epsilon$ = 36000)nm,

NMR (CDCL$_3$); $\delta$ 8.7 – 7.1 (m, 6H), 2.55 (s, 6H),

EXAMPLE 3

160 mg of 2,2'-diazidobiphenyl was dissolved in a small amount of diethyl ehter and then the solution thus obtained was dissolved in 500 ml of glycerol and the resultant solution was poured into a quarty cylindrical cell. The cell was dipped into a mixed coolant of ethyl alcohol and solid carbon dioxide to convert the solution to low-temperature rigid solution. The cell was irradiated with light in the same manner set forth in Example 1. After the irradiation, the cell was taken out of the coolant. After fluidized, the reaction product was extracted with 2l of diethyl ether. Diethyl ether was removed off by distillation. 62 mg of pure benzo[C]cinnoline was obtained by recrystallization of the residue using a mixed solvent of hexane and diethyl ether. Yield was about 52%.

EXAMPLE 4

200 mg of 2,2'-diazido-4-azabiphenyl was treated in the same manner as in Example 1 to obtain 7,9,10-triazaphenanthrene of 85% yield.

EXAMPLE 5

240 mg of 1-(2-azidophenyl)-2-azidonaphthalene was treated in the same manner as in Example 1 to obtain dibenzo[C]cinnoline of 80% yield.

What is claimed is:

1. Method for preparing benzo[C]cinnoline or its derivative which comprises irradiating a compound selected from 2,2'-diazidobiphenyl and its derivatives with light in a low-temperature rigid solvent.

2. Method according to claim 1 in which the starting compound has the general formula:

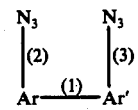

wherein Ar represents an aromatic group, Ar' represents an aromatic group, the bond (2) is present at the 2-position of Ar to the bond (1) and the bond (3) is present at the 2-position of Ar' to the bond (1).

3. Method according to claim 2 in which Ar and Ar' in the general formula are aromatic groups each of which is selected from the group of benzene ring and naphthalene ring.

4. Method according to claim 2 in which either or both of Ar and Ar' in the general formula have at least one substituent selected from the group consisting of hydrocarbon group, nitro group, carboxyl group, halogen atom, alkoxy group, acyl group, cyano group and sulfonic acid group.

5. Method according to claim 1 in which the low-temperature rigid solvent is selected from the group consisting of n-pentane, petroleum ether, diethyl ether, methyl alcohol, ethyl alcohol, isopentane, methyl cyclohexane, heptane, glycerol and mixtures thereof.

6. Method according to claim 1 in which the starting compound is 2,2'-diazidobiphenyl.

7. Method according to claim 1 in which the irradiation is conducted after the viscosity of the system become higher than 10$^3$ poise.

8. Method according to claim 1 in which the irradiation is conducted by using light of wavelength of about 200 nm to about 800 nm.

9. Method according to claim 1 in which the irradiation is conducted by using low-pressure mercury arc lamp.

* * * * *